US007087371B2

(12) United States Patent
Dobrinski et al.

(10) Patent No.: US 7,087,371 B2
(45) Date of Patent: Aug. 8, 2006

(54) MATERIAL AND METHODS FOR THE PRODUCTION OF SPERM AND ANALYSIS THEREOF

(75) Inventors: Ina Dobrinski, Chadds Ford, PA (US); Stefan Schlatt, Pittsburgh, PA (US); Ali Honaramooz, Kennett Sq., PA (US); Hans Scholer, Kennett Square, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 10/610,302

(22) Filed: Jun. 30, 2003

(65) Prior Publication Data

US 2004/0072141 A1 Apr. 15, 2004

Related U.S. Application Data

(60) Provisional application No. 60/392,945, filed on Jun. 28, 2002.

(51) Int. Cl.
*A01N 1/02* (2006.01)

(52) U.S. Cl. .................. 435/2; 435/325; 435/377; 424/93.7; 424/9.2

(58) Field of Classification Search .............. 435/2, 435/325, 374, 1.1, 1.3; 530/852; 424/93.7; 604/502; 623/23.72
See application file for complete search history.

(56) References Cited

U.S. PATENT DOCUMENTS

| 4,357,934 A | * | 11/1982 | Fahim .................... 600/33 |
| 4,929,542 A | * | 5/1990 | Risley ..................... 435/2 |
| 4,980,277 A | * | 12/1990 | Junnila .................... 435/2 |
| 5,627,066 A | * | 5/1997 | Gordon ................... 435/2 |
| 5,817,453 A | * | 10/1998 | Brinster ................. 435/1.1 |
| 5,859,307 A | * | 1/1999 | Mombaerts et al. ......... 800/9 |
| 5,872,230 A | * | 2/1999 | Stocco et al. ........... 536/22.1 |
| 6,107,540 A | * | 8/2000 | Sawyer et al. ............ 800/10 |
| 6,215,039 B1 |  | 4/2001 | Brinster |
| 2002/0131957 A1 | * | 9/2002 | Gavin et al. ........... 424/93.7 |

OTHER PUBLICATIONS

Johnson et al, "Effects of Developmental Age or Time after Transplantation on Sertoli Cell number and Testicular size in inbred fischer rats," 1996, Biol. Reprod., vol. 54, pp. 948-959.*

Deanesly, R, "Spermatogenesis and endocrine activity in grafts of frozen and thawed rat testis," 1954, J. Endocrinol, vol. 11 No. 2, pp. 201-206.*

Brinster et al, "Spermatogenesis following male germ-cell transplantation," 1994, Dev. Biol., vol. 91, pp. 11298-11302.*

(Continued)

*Primary Examiner*—Leon B. Lankford, Jr.
*Assistant Examiner*—Allison M. Ford
(74) *Attorney, Agent, or Firm*—Kathleen D. Rigaut; Robert C. Netter, Jr.; Dann Dorfman Herrell & Skillman

(57) ABSTRACT

Provided herein are methods of producing viable sperm from neonatal mammalian testes which have been engrafted in mice.

13 Claims, 7 Drawing Sheets

OTHER PUBLICATIONS

Figure 1:
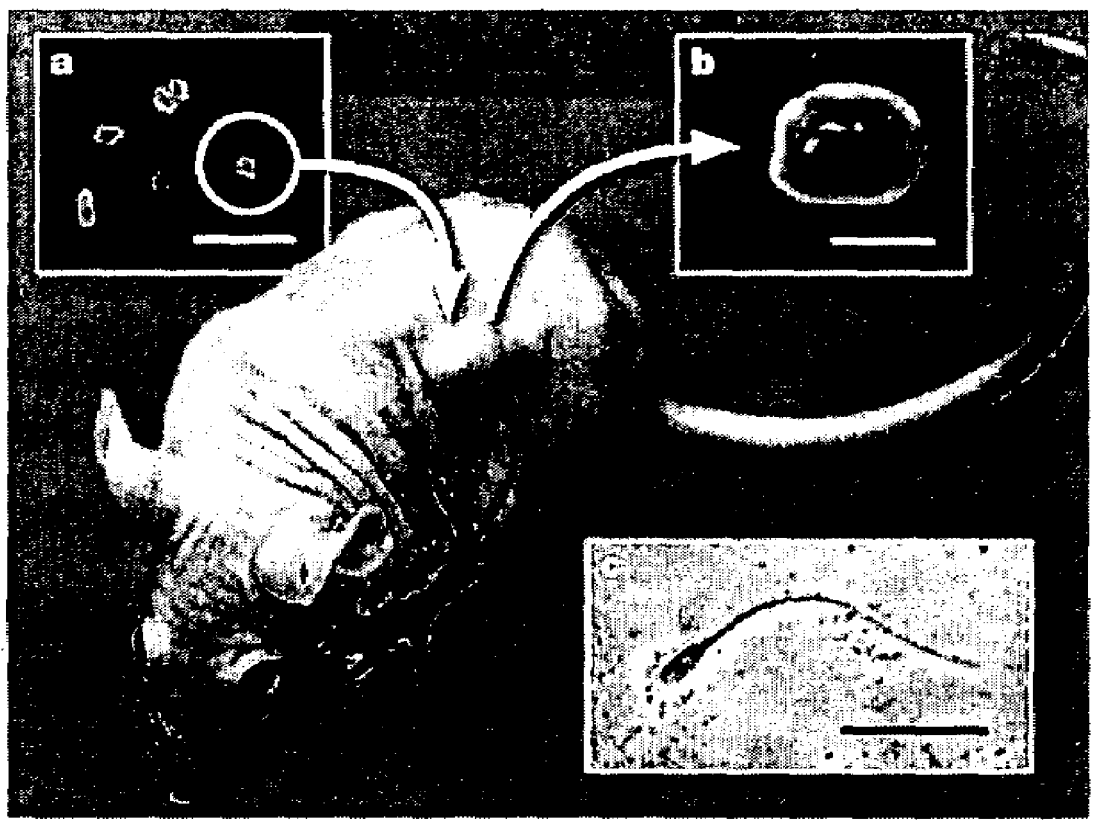

Bahadur, et al, "Testicular tissue cryopreservation in boys, Ethical and legal issues: Case Report," 2000, vol. 15, No. 6, pp. 1416-1420.*

Holstein et al, "Understanding spermatogenesis is a prerequisite for treatment, " 2003, Reproductive Biology and Endocrinology, vol. 1, pp. 107, www.rbej.com/content/1/1/107.*

"Animal Care and Use," University of Florida, 2000, www.iacuc.ufl.edu/OLD%20Web%20Site/immunodefmice.htm.*

Roscoe et al, "Failure of Spermatogenesis in Mice Lacking Connexin43," 2001, Biol. Reprod., vol. 65, pp. 829-838.*

Polge et al, "Revival of Spermatozoa after Vitrification and Dehydration at Low Temperatures," 1949, Nature, vol. 164, pp. 666.*

Research Animal Review, Mar. 1996, http://www.taconic.com/newsltrs/march96/march96.htm accessed Mar. 1, 2005.*

Bosma et al, Nature, 1983, vol. 301, pp. 527-530.*

Shinohara et al, Human Reproduction, Dec. 2002, vol. 17, No. 12, pp. 3039-3045.*

Bahadur et al, Human Reproduction, Jun. 2000, vol. 15, No. 6, pp. 1416-1420.*

Brinster, R.L., et al., "Germline transmission of donor haplotype following spermatogonial transplantation", Proc. Natl. Acad. Sci. U.S.A., vol. 91: p. 11303-11307, (1994).

Gosden, R., et al., "Preservation of fertility in nature and ART", Reproduction, vol. 123: p. 3-11, (2002).

Brinster, R.L., et al., "Spermatogenesis following male germ-cell transplantation", Proc. Natl. Acad. Sci. U.S.A., vol. 91: p. 11298-11302 (1994).

Honaramooz, A., et al., "Germ Cell Transplantation in Pigs", Biology of Reproduction, vol. 66: p. 21-28 (2002).

Van Pelt, A.M.M., et al., "Establishment of Cell Lines with Rat Spermatogonial Stem Cell Characteristics", Endocrinology, vol. 143: p. 1845-1850 (2002).

Schlatt, S., et al., "Germ cell transfer into rat, bovine, monkey and human testes", Human Reproduction, vol. 14: p. 144-150 (1999).

Ogawa, T., et al., "Xenogeneic Spermatogenesis Following Transplantation of Hamster Germ Cells in Mouse Testes", Biology of Reproduction, vol. 60: p. 515-521 (1999).

Nagano, M., et al., "Primate Spermatogonial Stem Cells Colonize Mouse Testes", Biology of Reproduction, vol. 64: p. 1409-1416 (2001).

Ogawa, T., "Spermatogonial transplantation: the principle and possible applications", J. Mol. Med., vol. 79: p. 368-374 (2001).

Schlatt, S., et al., "Male germ cell transplantation: an experimental approach with a clincial perspective", British Medical Bulletin, vol. 56: p. 824-836 (2000).

Ogawa, T., et al., "Transplantaion of male germ line stem cells restores fertility in infertile mice", Nature Medicine, vol. 6: p. 29-34, (2000).

* cited by examiner

| | | |
|---|---|---|
| 3A |  |  | 3B |
| 3C |  |  | 3D |
| 3E |  |  | 3F |

4A  4B
4C  4D
4E  4F

7A

7B

7C

MATERIAL AND METHODS FOR THE PRODUCTION OF SPERM AND ANALYSIS THEREOF

CROSS REFERENCE TO RELATED APPLICATION

This application claims the benefit of U.S. provisional application 60/392,945 filed Jun. 28, 2002, the entire disclosure of which is incorporated by reference herein.

Pursuant to 35 U.S.C. §202(c), it is acknowledged that the U.S. Government has certain rights in the invention described, which was made in part with funds from the USDA/NIH Grants Numbers 99-35205-8620, HD 39641-01, R01 RR 17359-01.

FIELD OF THE INVENTION

The present invention relates to the fields of xeno-transplantation, reproduction, and molecular biology.

More specifically, methods are provided for re-producing complete spermatogenesis by grafting xenogenic tissue from a variety of animal species, including humans, into mice.

BACKGROUND OF THE INVENTION

Several publications and patent documents are cited throughout the specification in order to describe the state of the art to which this invention pertains. Each of these references is incorporated herein as though set forth in full.

Improved treatments for many childhood cancers provide hope of long term survival for these patients. In the year 2000, it was estimated that 1 in 900 people aged 15–44 in the United States were cancer survivors (Bleyer WA., CA Cancer J Clin 1990; 40: 355–367). However, often the treatments used have long term negative effects, such as decreased fertility. A large study of childhood cancer survivors treated between 1945 and 1975 showed an adjusted relative fertility of 85% compared with that of their siblings. The adjusted relative fertility of male survivors was slightly lower than that of female survivors. The most dramatic declines in relative fertility rates were in male survivors who had been treated with alkylating agents (Byrne J, et al. N Engl J Med 1987; 317: 1315–1321). In one study of male children treated with alkylating agents for a variety of sarcomas, researchers found that 60% of participants had no sperm production, 29% had reduced sperm production, and only 12% had normal sperm counts. Higher doses of chemotherapy corresponded to lower sperm counts and poor morphology. All the patients who had been treated prior to puberty had abnormalities in their semen (Kenney et al., Cancer 2001; 613–621).

Spermatogenesis is a continuous, highly organized process that generates virtually unlimited numbers of sperm during adulthood. Many complex aspects of testis function in humans and large animals have remained elusive due to the lack of suitable in vitro or in vivo models.

Recent advances have opened new avenues for the study and preservation of gonadal function (Gosden R, et al. Reproduction 2002; 123:3–11). In the female, cryopreservation and grafting of the whole ovary or strips of ovarian tissue showed promising results in experimental studies, and might soon become a clinically useful strategy (Snow M, et al. Science 2002; 297:2227–2229; Wang X, et al. Nature 2002; 415:385–387; Picton H M, et al. Br Med Bull 2000; 56:603–615). In males, the advent of germ cell transplantation in mice (Brinster R L, et al. Proc Natl Acad Sci USA 1994; 91:11303–11307; Brinster R L, et al. Proc Natl Acad Sci USA 1994; 91:11298–11302), domestic animals (Honaramooz A, et al. Biol Reprod 2002; 66:21–28; Honaramooz A, et al. Mol Reprod Dev 2003; 64:422–428), and primates (Schlatt S, et al. Hum Reprod 1998; 14:144–150; Schlatt S, et al. Hum Reprod 2002; 17:55–62), the in vitro culture of male germ cells (Tesarik J, et al. Lancet 1999; 353:555–556), and the generation of immortalized cell lines from the male germ cell lineage (van Pelt A M, et al. Endocrinology 2002; 143: 1845–1850; Feng L X, et al. Science 2002; 297:392–395; Cooke H J et al. Nat Genet 2002; 32:90–91) are innovative tools leading to rapid scientific progress but are still at an experimental stage (Schlatt S, et al. Endocr Dev 2003; 5:136–155). Transplantation of spermatogonial stem cells from fertile donor mice to the testes of infertile recipient mice resulted in complete spermatogenesis (Brinster, R. L. et al. (1994) Proc. Natl Acad. Sci. USA 91, 11303–11307; Jiang, F. X. et al. Int. J. Androl. (1995) 18, 326–330; Ogawa, T., et al. Nature Med. (2000) 6, 29–34) and autologous transplantation was successful in the monkey (Schlatt, S. et al. Hum. Reprod. (1998) 14, 144–150) opening the field for medical applications (Schlatt, S., et al. Brit. Med. Bull. (2000) 56, 577–587). Cross-species transplantation of spermatogonial stem cells recovered from donor rats or hamsters to recipient mice resulted in the establishment of rat or hamster spermatogenesis in the mouse testis (Ogawa, T., et al. Biol. Reprod. (1999) 60, 515–521). However, transplantation of germ cells from phylogenetically more distant species including rabbits, dogs, pigs, bulls, horses and primates, including humans, into mouse testes, did not result in spermatogenesis beyond the stage of spermatogonial proliferation (Dobrinski, I., et al. Mol. Reprod. Develop. (2000) 57, 270–279; Nagano, M., et al. Biol. Reprod. (2001) 64, 1409–1416; Russell, L. D. et al. in Histological and Histopathological Evaluation of the Testis (eds Russell, L. D., Ettlin, R. A., SinhaHikim, A. P. & Clegg, E. D.) 1–40 (Cache River Press, Clearwater, 1990); Nagano et al., Fertil. Steril. (2002) 78(6):1225–33) likely due to the incompatibility of microenvironments.

Therefore a need exists in the art for a method of preserving fertility in prepubescent males who require chemotherapy, and for providing an improved model for study of testicular development and function.

SUMMARY OF THE INVENTION

Provided herein are methods of producing viable sperm from mammalian testes which have been engrafted into a recipient animal (e.g., a mouse). Accordingly, the instant invention provides means of producing an almost inexhaustible source of male gametes, even from immature gonads.

In particular, the instant methods provide reproductive options to prepubescent males who require a treatment which may impair their fertility.

In another aspect of the invention, means of preserving and producing sperm from endangered species or valuable livestock are provided.

In yet another embodiment of the invention, means of reproducing animals with a lethal phenotype are provided.

In a further embodiment of the invention, donor testicular tissue for engraftment in a recipient animal is provided. Preferably such grafts are approximately 0.5–1 mm$^3$ and comprise seminiferous tubules with Sertoli and germ cells which produce sperm after implantation into the recipient animal.

In yet another embodiment, sperm produced by the engraftment methods of the invention are provided. The use of sperm so produced for fertilization of an oocyte is also encompassed by the present invention, as are embryos produced using such sperm.

In yet a further aspect of the invention, methods for the identification of agents which alter spermatogenesis and/or sperm function are provided. Specifically, such methods may be used to identify and characterize contraceptive agents and additional therapeutic agents useful for the treatment of reproductive disease. Additionally, such methods may be employed to study reproductive toxicology.

BRIEF DESCRIPTIONS OF THE DRAWING

FIGS. 1A–C show grafting of testis tissue from newborn piglets under the skin of nude mice. The size of the pig testis grafts at the time of transplantation was about 0.5–1 mm in diameter (a) and expanded to 4–8 mm at 10 weeks after grafting (b), bar sizes: 5 mm. Most grafts from more advanced time points contained sperm. In c, a sperm extracted from a week 27 graft is shown, bar size: 20 µm.

Figure 2:
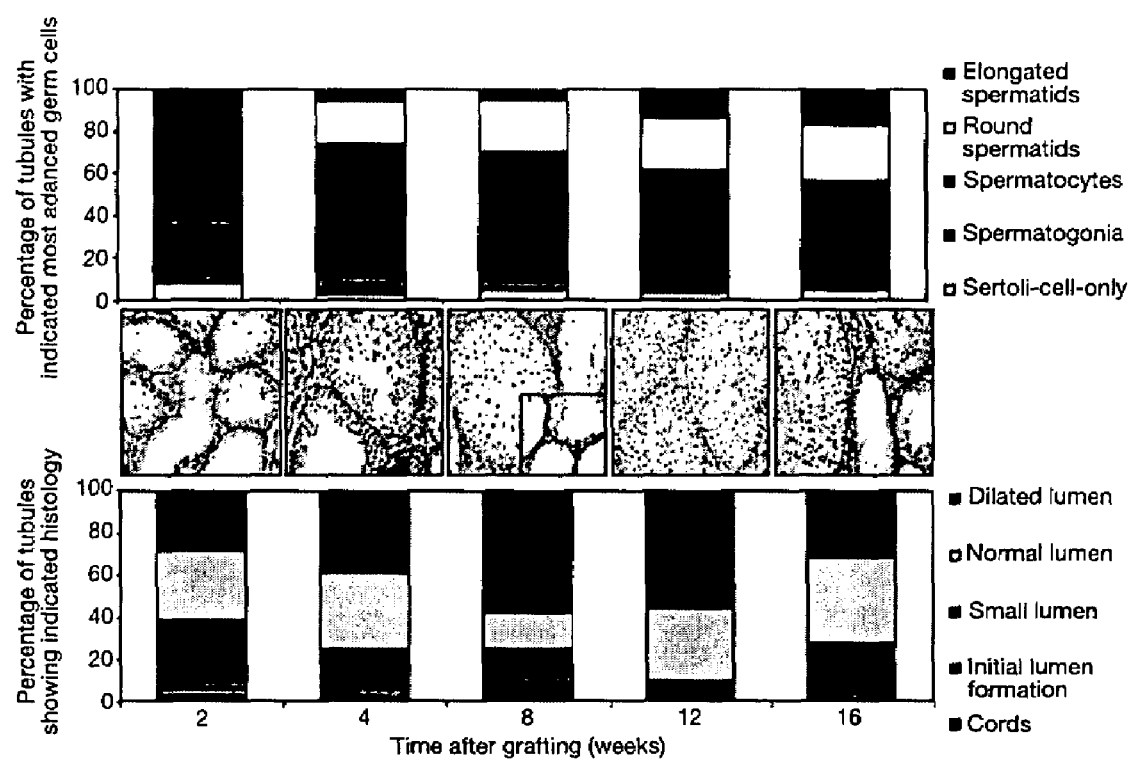

FIG. 2 shows histological evaluation of the developmental potential of newborn mouse testis tissue grafted under the back skin of nude mice. The upper panel illustrates the progression of spermatogenesis by showing the relative abundance of seminiferous tubules containing the indicated germ cell as the most advanced stage. The middle panel displays representative micrographs of the testicular grafts. The lower panel illustrates the progression of immature cords to fully differentiated seminiferous tubules showing the various degrees of lumen formation.

FIGS. 3A–3F show the histological appearance of pig or goat testis tissue before and after grafting into mice. Neonatal donor pig testis at the time of grafting (a), and grafted tissue at 12 weeks (b) or 18 weeks (c). Note the changes from seminiferous cords in (a) to fully developed seminiferous tubules with complete spermatogenesis (c). Asynchronous tubular development is apparent in a week 12 graft (b). Complete spermatogenic progression in a week 16 pig graft that was cryopreserved before grafting (d). One month-old donor goat testis at the time of grafting (e) and grafted tissue at week 10 (f), bar size: 100 µm.

FIGS. 4A–4F are a demonstration of sperm morphology and oocyte-activating competence of sperm from grafts of neonatal testes. Testicular sperm were isolated from (a) mouse-to-mouse, (c) pig-to-mouse or (e) goat-to-mouse testis grafts before intracytoplasmic sperm injection (ICSI) into mouse oocytes. Following ICSI, resumption of meiosis, polar body extrusion, and pronuclear formation were seen to occur within 6 hours. Mouse oocytes injected with sperm from any of the three species (b: mouse, d: pig and f: goat) displayed two pronuclei and a second polar body (Hoechst 33342 staining).

FIGS. 5A–5D show various procedures followed to obtain offspring from neonatal mouse testicular grafts. The testes from newborn pups were dissected and cut into halves about 0.5 mm² in diameter (A). Each half was used as one graft. Eight grafts per mouse were fixed to the s.c. muscle layer using small pieces of suture and were left in the mice for different time periods during which the growth of the testis tissue became visible through the back skin (B). At the time the mice were killed, the grafts had grown to a few millimeters in size (C). Sperm were retrieved from the grafted tissue and used for ICSI. The embryos obtained were transferred into pseudopregnant recipients, which gave birth to pups after a normal duration of pregnancy (D).

FIGS. 6A–6D show the histology of the testicular tissue before (A) and after (B–D) 4 wk of grafting. A) The seminiferous tubules of the neonatal mouse testis contain only Sertoli cells and gonocytes. Periodic acid-Schiff-hematoxylin. Bar=10 µm. B) Low-power view of the grafted testicular tissue in direct contact with the muscle layer of the skin. BrdU incorporation was detected by immunohistochemistry (nuclear precipitate) and indicates high proliferative activity in papilla of the hair and in premeiotic germ cells. A distention of the tubular lumen is visible in many seminiferous tubules. Hematoxylin counterstain. Bar=250 µm. C) High-power view of the same graft shown in B. All stages of germ cells are present 4 wk after grafting. Numerous BrdU-positive cells (arrows) are visible in cells lying on the basement membrane of the seminiferous tubules. Hematoxylin counterstain. Bar=50 µm. D) Immunohistochemical detection of alpha smooth muscle actin of a section adjacent to that shown in C. Blood vessels and peritubular cells have a positive signal (brown precipitate), indicating final differentiation into smooth muscle cells. Hematoxylin counterstain. Bar=50 µm.

FIGS. 7A–C show endocrine parameters determined in the nine experimental mouse groups (n=5). Asterisks indicate a significant difference in comparison with the castrated controls ($P<0.05$). Serum FSH levels were significantly lower than castrate levels after 2 and 4 wk and remained in the intermediate range at Weeks 8–16 (a). The androgens levels were estimated using the weight of the seminal vesicles (b) and the serum levels of testosterone (c). Both parameters show that the grafts produced normal to high physiological androgen levels from Week 8 to Week 16 in the recipient mice.

DETAILED DESCRIPTION OF THE INVENTION

The instant invention provides compositions and methods for establishing complete spermatogenesis by grafting testis tissue harvested from a mammal of interest (e.g. newborn mice, pigs, goats, sheep, domestic animals, non-human primates, rare or endangered species, or humans) into mouse hosts. This novel approach maintains structural integrity and provides a superior in vivo model for the study and manipulation of testis function, as well as for male germ line preservation. Surprisingly, this approach is applicable to diverse mammalian species.

Also provided herein is experimental evidence demonstrating that the sperm isolated from the testis grafts also direct embryonic development. Histological and hormonal assays were used to determine the best time point for retrieval of sperm following the grafting procedure. Combining sperm retrieval from testicular tissue, intracytoplasmic sperm injection (ICSI), embryo culture, and transfer in vivo, live offspring were obtained from the sperm produced in mouse neonatal grafts. This result demonstrates that an ectopic location, such as the skin, provides an adequate environment for orchestration of gametogenesis from unprimed testicular tissue.

Additionally, the methods of the instant invention produce accelerated testicular development, in certain case, providing spermatogenesis sooner than that observed in a normally developing animal.

I. Definitions

The following definitions are provided to facilitate an understanding of the present invention:

"Ectopic Grafting" refers to grafting into an a typical place. For example, testes tissue grafted subcutaneously.

As used herein the term "engrafted" refers to tissue surgically implanted at any anatomical site under conditions such that the host may maintain said tissue.

"Xenografting" generally means grafting tissue from one species to another.

A "donor" is any male animal whose germ line is to be preserved. Such animals include, but are not limited to a mouse, a rat, a dog, a cat, a horse, a sheep, a bull, a llama, a pig, a non-human primate, a human, a rare or endangered species, a domestic animal, and livestock.

A "recipient" is any animal which receives a tissue graft. A recipient may be an animal of the same species as the donor, but is preferably an animal of a different species (so the graft is a xenograft). In another embodiment, a "recipient" is immunocompromised. Alternatively, the "recipient" is an immunocompromised rodent, such as an athymic, SCID or RAG mouse. The recipient may optionally be castrated.

"Rare or endangered species" include but are not limited to any animal listed by any organization as being threatened or endangered, or any animal whose population, or habitat is threatened, or any animal which is desirably breed in captivity. For example, lists of endangered species may be found as http://endangered.fws.gov.wildlife.html.

As used herein "immunocompromised" refers to an animal with an immune system rendered deficient relative to a normal animal by breeding, by an immunodeficiency disorder, or by the administration immunosuppressive agents.

"Cryopreserving" is the process of freezing tissue for preservation. Numerous techniques of cryopreservation are generally known in the art, and provided for example in U.S. Pat. Nos. 5,942,437 and 6,361,934. Preservation of the male germ line may be accomplished by freezing sperm or, in situations where mature sperm cannot be obtained, by cryopreservation of testis cells or tissue. Cryopreservation of testis tissue has the advantage of maintaining structural integrity and providing a compatible microenvironment needed for completion of spermatogenesis after xenotransplantation.

A "suitable culture medium" includes any medium which allows maintenance of viable tissue or cells, including without limitation, Dulbeccos modified Eagle medium, HAMS F12, supplemented with serum etc. Such mediums also include the cryopreservation media described herein.

"Pre-pubescent" refers to an animal which is not yet capable of reproduction. Specifically, a prepubescent male is not yet capable of spermatogenesis.

"Male fertility" means the ability of a male to produce sperm which is capable of fertilizing an oocyte.

"Sperm quality" refers to the ability of sperm to fertilize an oocyte, and can be measured by characteristics including but not limited to sperm viability, sperm number, and sperm morphology.

"Fertility impairing treatment" includes but is not limited to any treatment, medical or otherwise which impairs or prevents spermatogenesis or germ cell differentiation.

"Differentiation" can refer to the development or maturation of tissue. For example, immature testicular tissue differentiates into tissue capable of spermatogenesis. The various stages of such differentiation are described for example in Russell, L. D. et al. in Histological and Histopathological Evaluation of the Testis (eds Russell, L. D., Ettlin, R. A., SinhaHikim, A. P. & Clegg, E. D.) 1–40 (Cache River Press, Clearwater, 1990).

II. Methods of Producing Sperm from Neonatal or Immature Mammalian Testes Engrafted in Mice or Other Suitable Hosts Testes tissue is isolated from an appropriate mammal. For example, tissue may be isolated from a prepubescent male who will undergo chemotherapeutic therapy. Alternatively, tissue may be harvested from a male of an endangered species or from valuable livestock. Or, tissue may be harvested from an animal with a lethal phenotype.

This tissue is then grafted into a suitable non-host animal. A variety of non-human animals can be used as the graft recipient, including but not limited to vertebrates such as rodents, non-human primates, ovines, bovines, ruminants, lagomorphs, porcines, caprines, equines, canines, felines, aves, etc. Preferred non-human animals include the rat and mouse, and immune compromised mice are particularly preferred.

The testicular graft described above may be implanted in a variety of spaces in a non-human host. It is not intended that the present invention be limited to a specific location. Such spaces include, but are not limited to the peritoneum, the thoracic cavity, the renal capsule, the anterior chamber of the eye, the brain, or the subcutaneous space. Preferably, the subdermal space of the dorsal aspect of the host is utilized.

Xenograft materials may be chemically treated to reduce immunogenicity and increase stability prior to implantation into a recipient. Xenograft tissues may also be subjected to various physical treatments in preparation for implantation. For example, tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660.

The following non-limiting examples are provided to further illustrate the present invention.

EXAMPLE 1

Xenograft of Neonatal Mammalian Tissue in Mice

This example describes the removal of neonatal testes tissue from mice, pigs, and goats, grafting of that tissue into mice, and subsequent differentiation of the tissue into mature testicular tissue wherein spermatogenesis occurs.

Materials and Methods

Donor Testis Tissue

Mouse donor testes were obtained from 1- to 2-day old ICR or B6C3 $F_1$ pups. Testes were cut in half and each half served as a graft. Pig and goat testes were obtained from routine castration of 1-week or 4-week old animals, respectively. Small fragments of these testis tissues (about 0.5–1 mm$^3$) were prepared. Before grafting into recipient mice, all testis fragments were maintained in Dulbecco's Modified Eagle's Medium (DMEM) on ice.

Comparable tissue pieces were fixed at the time of grafting to serve as reference for graft development.

Experimental Surgery

Six-week old male immunodeficient NCr nude mice (Taconic, Germantown, N.Y.) were anesthetized and castrated, and then received eight transverse linear incisions (about 0.5–1 cm in length) into the dorsal skin. A fragment of the testis tissue was affixed subcutaneously near the incision with braided silk surgical suture and the incisions were closed with wound clips (Michel Clips 7.5 mm, Miltex, Bethpage, N.Y.). Sham-operation was performed on groups of intact and castrated mice as controls.

Sample Processing and Microscopy

At the time of sacrifice, the mice were anesthetized and bled by heart puncture. The serum was kept frozen until analysis for hormone levels. Surviving grafts were fixed in Bouin's solution and stored in 70% ethanol until processing for histology. The weight of seminal vesicles was documented. The following histological analyses were performed: photographic documentation of the histology, measurement of seminiferous tubule diameter, evaluation of the relative number of seminiferous tubules showing differentiation, and determination of the type and prevalence of the most advanced germ cells.

Isolation and Storage of Sperm from Excised Grafts

To obtain sperm from excised testis grafts, the tissue was minced and dispersed in Whittingham medium at 4° C. (Fraser, L. R. et al. Biol. Reprod. (1975) 13, 513–518). The medium was supplemented with bovine serum albumin (BSA, 3% w/v) (Wakayama, T., et al. J. Reprod. Fertil. (1998) 112, 11–17). The crude cell suspension was either used fresh (see below), or aliquoted in cryovials, snap-frozen in liquid nitrogen and maintained at −196° C.

Intracytoplasmic Injection of Sperm into Mouse Oocytes (ICSI)

Metaphase II mouse oocytes and sperm from mouse, pig and goat grafts were micromanipulated in HEPES-buffered CZB medium (with glucose, BSA-free, PVP 1% w/v) (Chatot, C. L., et al. Biol Reprod. (1990) 42, 432–440) using a piezo actuator (Prime-Tech, Ibaraki, Japan) and DIC optics (Nikon) at 28° C. Briefly, individual sperm were aspirated into a 10 μm inner diameter (i.d.) blunt-end borosilicate microcapillar loaded with mercury. In case of the mouse sperm, application of 1–5 piezo pulses to the neck region, held at the tip of the capillary, allowed partition of the sperm head from the tail. The sperm or sperm head was immediately injected deep into the oocyte along with a minimal amount of carrier medium. The injected oocytes were allowed to recover in the micromanipulation drop on the stage of the microscope for 15 minutes, then transferred to culture medium (M16) and incubated at 37° C. under 5% $CO_2$ in air. As an indication of the sperm functional competence, the extrusion of the oocyte's second polar body and formation of the sperm-derived pronucleus was monitored by DNA staining with Hoechst 33342, at 2 and 8 hours post ICSI (Goud, P. T., et al. Hum. Reprod. (1998) 13, 1336–1345).

Storage and Cryopreservation of Testis Tissue

Testes of piglets were either maintained at 4° C. in saline solution for two days, or were cut into small fragments and subjected to immersion in fetal bovine serum, Dulbecco's modified Eagle's medium, and dimethyl sulfoxide at a 1:3:1 ratio, and cooling in an alcohol bath to provide a rate of −1° C./min to −70° C., before storing at −196° C. (Dobrinski, I., et al. Biol. Reprod. (1999) 61, 1331–1339; Dobrinski, I., et al. Mol. Reprod. Develop. (2000) 57, 270–279)

Comparison of the Viability and Developmental Potential of Porcine Testicular Tissue After Preservation by Different Methods of Cryopreservation or Short-term Refrigeration Small fragments of testis tissue from 1-wk old piglets and 3-mo old boars were prepared. Four preservation methods included: 1) Automated slow freezing protocol involving immersion in Leibovitz medium containing 2% bovine serum albumin and 10% dimethyl sulfoxide (DMSO), cooling at −2° C./min from 20° C. to 4° C.; 0.3° C./min from 4° C. to −30° C.; and −50° C./min from −30° C. to −130° C., and storing in a LN2 freezer; 2) Conventional slow freezing protocol established for isolated germ cell suspensions using fetal bovine serum (FBS), Dulbecco Modified Eagle Medium, and DMSO at a 1:3:1 ratio, and a Nalgene alcohol bath container to provide a rate of 1° C./min to −70° C., before storing in a LN2 freezer; 3) Vitrification involving processing through a solution containing DPBS with 10% FBS, 10% glycerol and 20% ethylene glycol, then DPBS with 10% FBS, 25% glycerol and 25% ethylene glycol, 15 min each, followed by plunging into LN2; 4) Refrigeration at 4° C. for 2 days.

Hormone Analysis

Serum levels of testosterone were measured by heterologous radioimmunoassay after double-extraction (Chandolia, R. K. et al. Acta. Endocrinol. (1991) 125, 547–555). Intra- and inter-assay variations were 5.0 and 8.2%, respectively. Circulating concentrations of FSH were determined by a commercially available system (Rat FSH Assay System, Amersham Pharmacia, Piscataway, N.J.), following the instructions of the supplier without magnetic separation. Intra- and inter-assay variations were 5.6 and 5.1%, respectively.

Results/Discussion

Fragments of testicular tissue (0.5–1 $mm^3$ in size) from neonatal mice, pigs or goats were grafted under the back skin of castrated immunodeficient mice. Groups of recipient mice were sacrificed after grafting at 2–4 week intervals and the status of graft survival and spermatogenesis were assessed. Overall, more than 60% of the neonatal testicular grafts from all three donor species survived. All recovered grafts had increased in volume, some more than 100 times, and ultimately produced mature sperm (FIG. 1). The recipient mice (n=94), some kept as long as a year, did not show signs of illness or evidence of neoplasia in any of the recovered grafts (n=477).

Histological analysis revealed full differentiation of the mouse testis allografts. Complete spermatogenesis was observed in the grafts of newborn murine testis, originally containing primitive gonocytes as the only type of germ cells (Orth, J. M. in Cell and Molecular Biology of the Testis (eds Desjardins, C. & Ewing, L. L.) 3–42 (Oxford University Press, New York, 1993)) (FIG. 2). The kinetics of spermatogenic progression were identical to the intact mouse testis (McCarrey, J. R. in Cell and Molecular Biology of the Testis. (eds Desjardins, C. & Ewing, L. L.) 58–89 (Oxford University Press, New York, 1993)) with spermatocytes as the most advanced germ cells observed after two weeks and the first round of spermatogenesis being complete four weeks after grafting. However, in many seminiferous tubules a dilation of the lumen accompanied by a disorganized epithelium and premature sloughing of postmeiotic germ cells was evident, likely as a result of the block of fluid flow (Eddy, E. M. et al. Endocrinology (1996) 137, 4796–4805; Lee, K-H. et al. Biol. Reprod. (2000) 63, 1873–1880).

Figure 3:
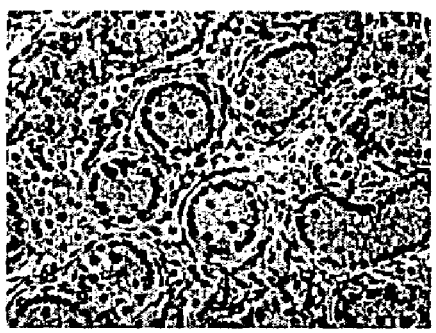
Figure 3:
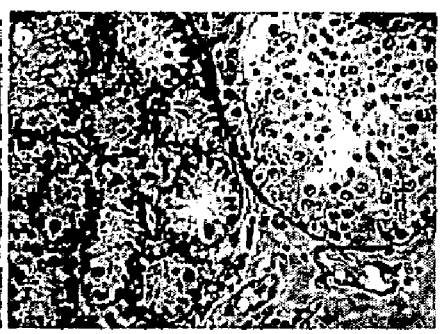
Figure 3:
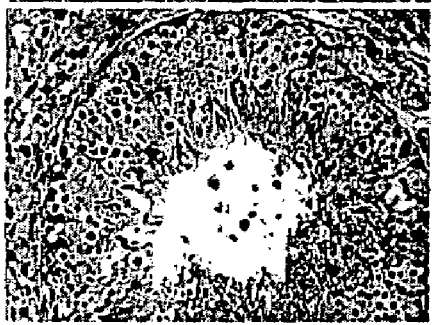
Figure 3:
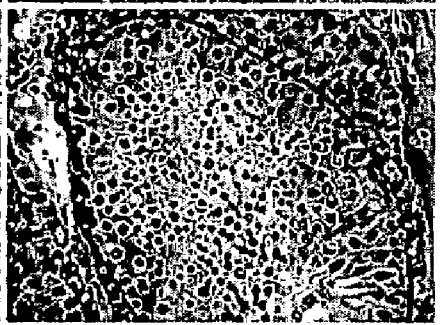
Figure 3:
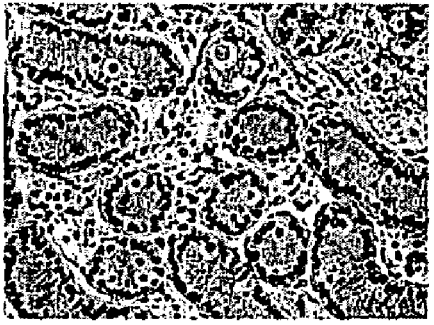
Figure 3:

Xenografting of newborn pig testis fragments into mice resulted in complete spermatogenesis following the developmental patterns of pig testis. There was a gradual progression from the primitive seminiferous cords (FIG. 3a) into fully developed seminiferous tubules with all stages of spermatogenic cells present (FIGS. 3b, c). Surprisingly, in contrast to xenotransplantation of isolated testicular cells (Dobrinski, I., et al. Mol. Reprod. Develop. (2000) 57, 270–279; Nagano, M., et al. Biol. Reprod. (2001) 64, 1409–1416; Russell, L. D. et al. in Histological and Histopathological Evaluation of the Testis (eds Russell, L. D., Ettlin, R. A., SinhaHikim, A. P. & Clegg, E. D.) 1–40 (Cache River Press, Clearwater, 1990), xenografting of pig testis fragments led to the production of sperm. Compared to the pig testis, spermatogenesis developed earlier in grafted tissue. Round spermatids were first present at 12 weeks after grafting, whereas in the pig they appear at or after 14 weeks of age. In addition, the diameter of seminiferous tubules increased faster in grafts; at week 8 it was about 120 µm (range 72–187 µm), compared to about 56 µm (range 47–67 µm) in intact pig testes. Some tubules displayed asynchronous development (FIG. 3b), which was not observed in mouse-to-mouse grafts. In contrast to mouse grafts, pig grafts examined at much later time points (up to a year) contained mostly complete, morphologically normal spermatogenesis, with the number of sperm per gram (e.g., $112 \times 10^6$ sperm isolated from a 0.75 gram graft) comparable to that in intact pig testes (Amann, R. P. in The Testis. (eds Johnson, A. D., Gomes, W. R., & Vademark, N. L.) 433–482 (Academic Press, New York, 1970); Swierstra, E. E. J. Reprod. Fertil. (1968) 17, 459–69; Swierstra, E. E. J. Reprod. Fertil. (1971) 27, 91–99).

Goat testis xenografts also developed from an immature state (FIG. 3e) to full spermatogenesis with seminiferous tubules displaying normal stages of goat germ cell development (FIG. 3f). Mature and viable sperm could also be isolated from the grafts in high concentrations (e.g., $67 \times 10^6$ sperm/gram).

Figure 4:
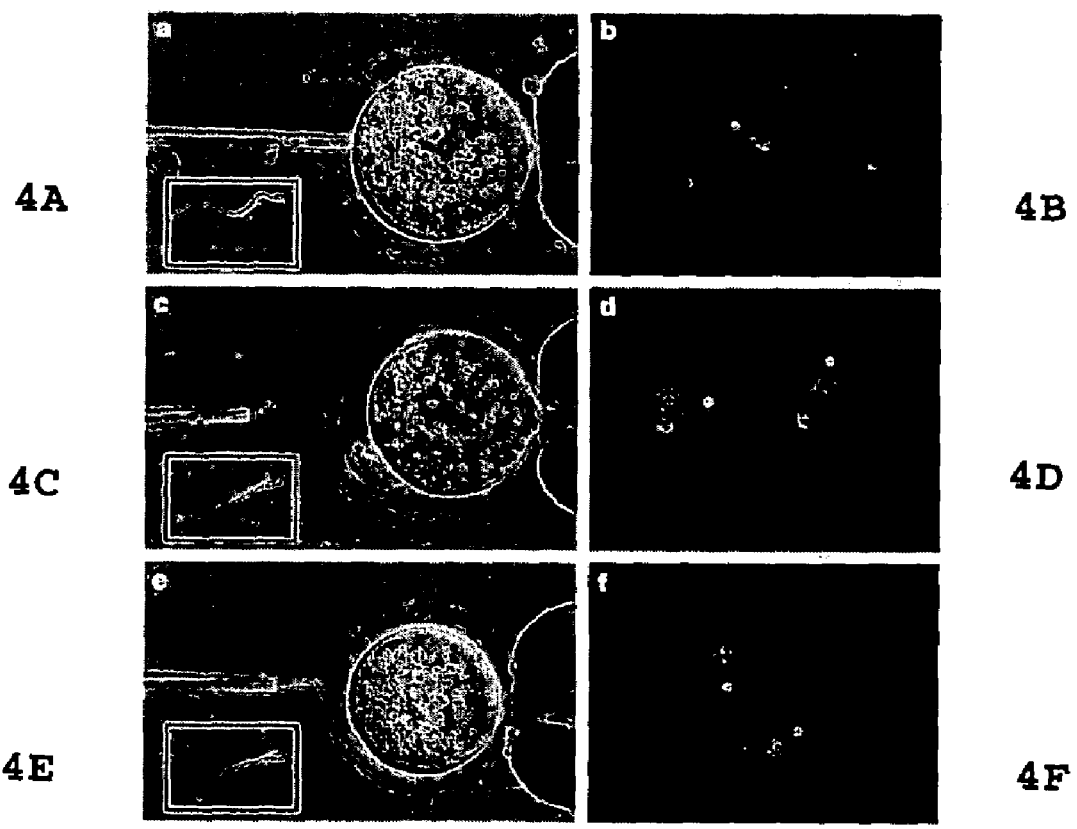

Sperm recovered from testis grafts of all three species into mice were viable and functional, as shown by fertilization after intracytoplasmic injection (ICSI) into mouse oocytes (FIG. 4). Furthermore, homologous mouse embryos produced using this system showed normal fetal development after transfer into pseudopregnant mice. The production of mature and functionally competent sperm from three phylogenetically different species indicates that testis tissue grafting will be applicable to a wide variety of mammalian species.

The foregoing data demonstrate initiation and completion of spermatogenesis in fresh testicular tissue grafted into mice. To extend this powerful approach to situations in which grafting of freshly harvested tissue is not possible, cooling or cryopreservation of pig testis fragments prior to grafting was investigated. Automated slow freezing, conventional slow freezing, vitrification, and refrigeration were used. Trypan blue exclusion was used to assess viability of single cell preparations after enzymatic digestion of the preserved testis fragments. Viability of cells from the vitrification protocol was less than 33%, while that of the other protocols was more than 60%. Four weeks after transplantation into immunodeficient mice, graft survival with subsequent differentiation was observed for all protocols except vitrification. In all groups with surviving grafts, graft size increased more dramatically with newborn donor tissue. These results indicate that porcine testis tissue can be successfully stored by refrigeration for 2 days or cryopreserved using slow-freezing protocols prior to transplantation. Indeed, testis tissue preserved by refrigeration for up to 2 days or by cryopreservation for longer periods maintained the potential to develop complete spermatogenesis and steroidogenesis when grafted into mice (FIG. 3d). This observation makes the technique immediately applicable to a clinical or field situation.

Normal spermatogenesis requires the combined effects of gonadotropins (FSH and LH), androgens and possibly other hormones. The endocrine function of the testis is controlled by feedback loops known as the hypothalamic-pituitary-gonadal axis. Testosterone released from Leydig cells, together with inhibin secreted from Sertoli cells, negatively control the release of FSH and LH from the pituitary. In castrated animals and in the absence of testosterone, serum levels of FSH and LH increase dramatically. The results from both allografts and xenografts indicate that the feedback loop to control the release of FSH is initiated in grafted mice since the serum levels of FSH were significantly lower than in castrated mice and remained at intermediate levels between the intact and castrate range. In mouse-to-mouse grafts, increasing damage to the seminiferous epithelium from fluid stasis may diminish the feedback from the grafted tissue and cause FSH serum levels to reach castrate levels after week 8. This was not observed in recipients of xenografts. In all recipient mice, a stable and functional feedback loop exists between the pituitary of the host and the Leydig cells in the allografts or xenografts, as becomes evident by a significant increase in the weight of the seminal vesicles (highly androgen dependent and thereby a reliable bioassay for androgens) and by the significantly increased levels of serum testosterone compared to castrated control animals. This indicates that the grafts fully supplement androgens to the castrated recipients.

The completion of spermatogenesis in testis xenografts originating from neonatal pigs and goats indicates that it is feasible to initiate and maintain spermatogenesis in a phylogenetically distant species. Murine gonadotropins effectively support the development, differentiation and maintenance of these testicular xenografts despite species-specificity, and exogenous hormone supplementation is not needed. There are several immediate, highly relevant applications for testis tissue grafting: First, testis grafting represents a new option for male germ line preservation. In contrast to the conventionally used method of sperm cryopreservation, this procedure provides a potentially inexhaustible source of male gametes, even from immature gonads. Unlike autologous transplantation of isolated germ cells to restore fertility in a patient following cancer therapy, xenologous grafting and use of the resultant sperm for assisted fertilization will eliminate the potential risk of tumor cell transmission. Second, grafting of fresh or preserved testis tissue offers an invaluable tool for the conservation of endangered species or valuable livestock by allowing sperm production from immature males. Third, the accessibility of the tissue in the mouse host makes it possible to manipulate spermatogenesis and steroidogenesis in a controlled manner that is not feasible in the donor animal and certainly not in humans. This in turn will allow analysis of the effects of toxicants and potential male contraceptives on testis function in the target species. Fourth, grafting of testis tissue from experimental animal strains will provide geneticists with a previously unavailable tool to study germ cell development and even to produce gametes from animals with poor viability, such as neonatal lethal transgenic, mutant or cloned animals.

EXAMPLE II

Progeny from Sperm Obtained After Ectopic Grafting of Neonatal Mouse Testes

Progeny were successfully produced using sperm from engrafted testes tissue. Additionally hormone levels were successfully regulated by the grafts in castrated mice.

Materials and Methods

Animals and Experimental Surgery

Figure 5:
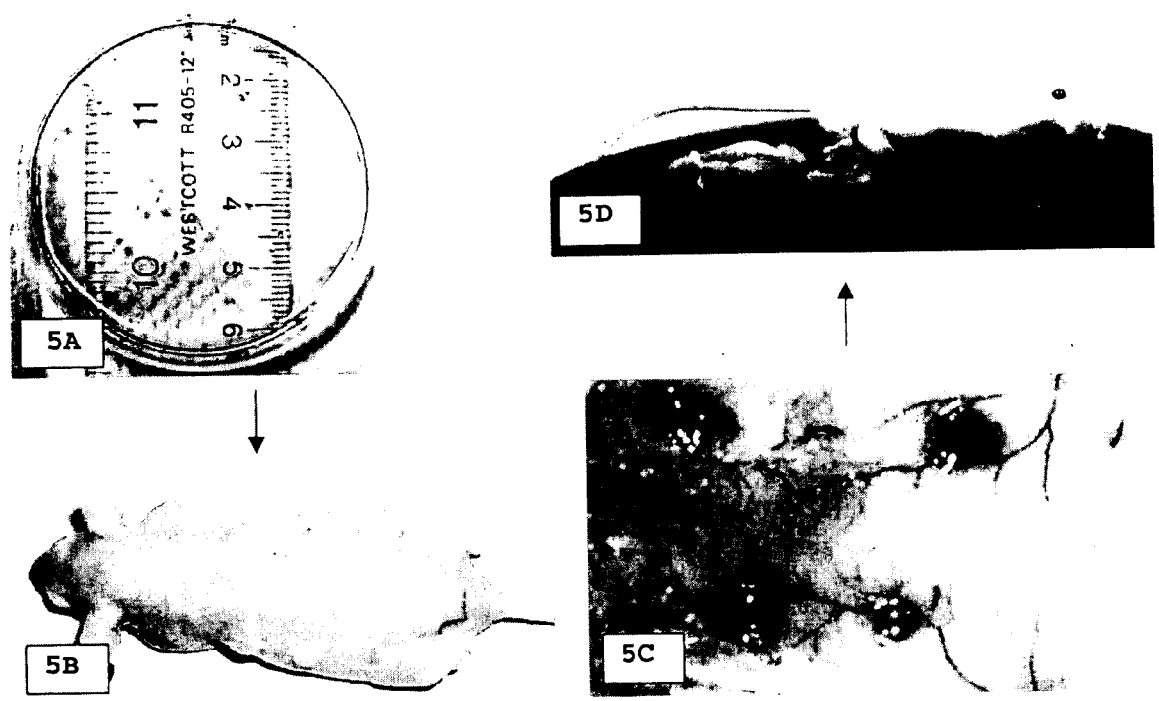

Donor testes were dissected from neonatal ICR or B6C3 F$_1$ (C57BL/6×C3H/He) pups, which were killed by decapitation. A total of 120 male pups were used for the experiment. Testes were cut in half (the size of the fragments ranged from 0.5 to 1 $mm^3$) and kept in ice-cold Dulbecco modified Eagle medium until grafting, which occurred within a maximum of 1.5 h. The various steps and outcomes of the procedure are indicated in FIG. 5. Some testes fragments were fixed in Bouin solution immediately after dissection to serve as a reference for testis development.

Five- to 7-wk-old male immunodeficient NCr mice (Taconic, Germantown, N.Y.) were used as recipients (n=44). For testis grafting, anesthesia was induced and maintained using Avertin (2,2,2-tribromoethanol; 63 g/kg body weight). The animals were castrated through scrotal incisions. The scrotal skin was closed using Michel stainless steel wound clips. Four skin incisions 4–5 mm each were made on either side of the dorsal midline. Using nonabsorbable 6/0 prolene suture (Ethicon, Somerville, N.Y.), eight grafts per recipient were secured to the muscle layer of the skin. The wounds were closed with Michel clips. Throughout the experiment, the mice were kept in groups of 5–7 per cage, with food and water available ad libitum.

Recipient mice were randomly distributed among nine experimental groups. In groups 1–5, castrated recipients receiving grafts were analyzed at weeks 2, 4, 8, 12, and 16 (n=5 mice/group), in groups 6 and 7, castrated controls were killed at week 4 (n=4) and week 12 (n=5), and in groups 8 and 9, intact controls were killed at the start of the experiment (n=5) and at week 12 (n=5). Two hours before death, the animals received an i.p. injection of bromodeoxyuridine (BrdU, 100 mg/kg body weight). At the time of death, the mice were weighed and anesthetized, and blood was collected by cardiac puncture. The seminal vesicles were dissected and weighed, the back skin was removed and photographed, and the number of visible grafts was recorded. The testicular tissue was dissected from the skin and fixed in Bouin solution. All animal experiments were approved by and performed under the guidance of the Animal Care and Use Committee at the University of Pennsylvania.

Histology and Microscopy

Tissue was fixed for 18–24 h in Bouin solution, transferred for storage into 70% ethanol, and embedded in paraffin for sectioning at 5 μm. Tissue sections were stained with hematoxylin and eosin. BrdU was localized by immunohistochemistry. Sections were deparaffinized and rehydrated. After rinsing with tap and distilled water, sections were hydrolyzed using 1 M HCl at 70° C. for 8 min in a temperature-controlled microwave oven. After a wash in running tap water, the sections were incubated for 15 min at room temperature in 0.1% trypsin in Tris-buffered saline (TBS: 10 mM Tris, 150 mM NaCl, pH 7.6). Using 5% normal goat serum, nonspecific staining was blocked for 20 min immediately before incubation with a monoclonal mouse anti-BrdU antibody (M0744; DAKO, Carpinteria, Calif.; diluted 1:30 in TBS+0.1% BSA) for 60 min or overnight. After three washes in TBS, sections were incubated with secondary, goat anti-mouse IgG linked to horseradish peroxidase for 60 min. After several washes in TBS, the label was visualized using diaminobenzidine as a substrate to be converted into a dark brown precipitate. The reaction was stopped by a rinse in distilled water. Slides were then counterstained with hematoxylin, dehydrated, and mounted. A similar protocol without the hydrolysis and digestion steps was used for staining of alpha smooth muscle actin using a commercially available antibody (A2547; Sigma, St. Louis, Mo.). Tissue sections were qualitatively analyzed for the degree of spermatogenic activity and the most advanced stage of germ cell development achieved at the various time points analyzed. Representative tissue sections were photographed.

RIA for Testosterone and FSH

Testosterone levels were measured using a previously published RIA (Chandolia R K, et al. Acta Endocrinol 1991; 125:547–555). Each sample was processed in duplicate after double extraction with diethyl ether. Intra- and interassay variances were 5.0% and 8.2%, respectively. FSH was determined by a commercially available rat assay system (Amersham, Pharmacia, Piscataway, N.J.) without magnetic separation. Intra- and interassay variations were <6%. One-way ANOVA followed by a Tukey multiple comparison test was performed to determine statistical significance of differences in hormone measurements and weights of seminal vesicles. Data were expressed as means±SEM. Differences were considered significant at $P<0.05$.

Preparation of Sperm Samples and Assisted Fertilization

Sperm were retrieved from the testicular grafts after mincing and dispersing the tissue in Whittingham medium supplemented with BSA (3% w/v). The sperm were used for assisted fertilization either fresh or after cryopreservation (snap frozen in liquid nitrogen). Sperm were partitioned into a head and a tail, and the head was injected into metaphase II mouse oocytes with a 10-mm blunt-end borosilicate capillary using a piezo actuator (Prime-Tech, Ibaraki, Japan) under observation by DIC optics (Nikon, Tokyo, Japan). Oocytes were maintained in Hepes-buffered CZB medium supplemented with glucose and polyvinylpyrrolidone (1% w/v) and allowed to recover after injection for 15 min, when they were transferred into culture medium M16 and further cultured at 37° C. in 5% CO2 in air. Oocyte activation after ICSI was measured by the second polar body extrusion occurring 2–3 h later. Seventy-one embryos (from the 144 total zygotes obtained after fertilization) were transferred at the two-cell stage (n=50) and the blastocyst stage (n=21) to the uterus of two pseudopregnant females at 0.5 days postcoitum (dpc) (two-cell embryos) and two pseudopregnant females at 2.5 dpc (blastocysts). One female from each group delivered pups.

RESULTS

Evaluation of Testicular Growth

Growth of the grafted testicular tissue was easily observed under the back skin of the nude mice (FIG. 5B). At the time of death, the skin was stretched and photographed to document the survival and growth of the grafts. FIG. 5C shows a typical example of the back skin, with four of eight grafts recovered after 4 wk. About 60% of all grafts survived and grew to a typical size of 4–6 mm in diameter.

Evaluation of Testicular Differentiation

Figure 6:
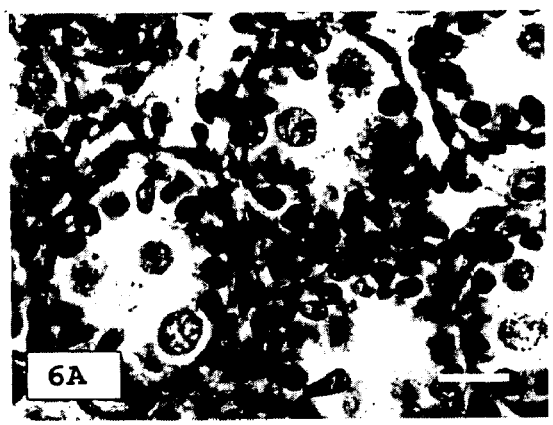
Figure 6:
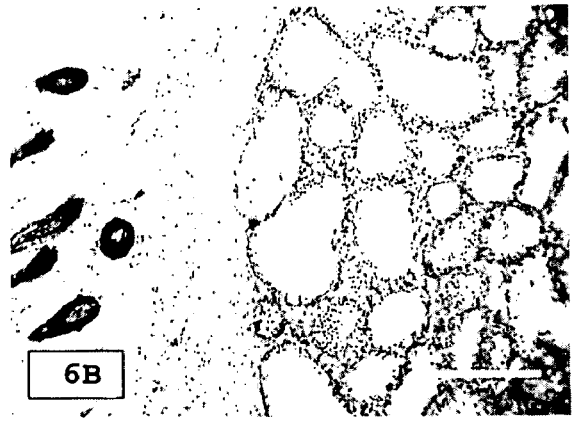
Figure 6:
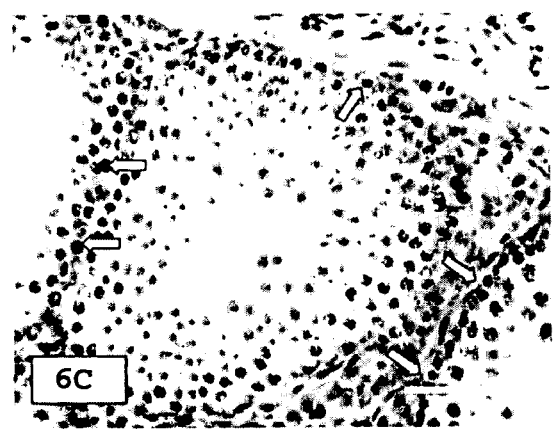
Figure 6:
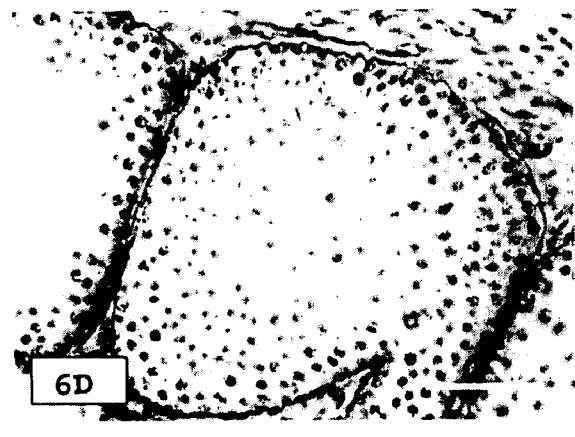

At the time of grafting, the testicular tissue consisted of seminiferous cords; Sertoli cells and gonocytes were the only cells present (FIG. 6A). Two weeks after grafting, 60% of the seminiferous tubules contained spermatocytes. Round spermatids were seen in about 20% of the tubular tissue at 4 wk after grafting, and a few tubules already contained elongated spermatids. A typical example of well developed seminiferous tissue showing numerous proliferatively active premeiotic germ cells and fully differentiated peritubular cells 4 wk after grafting is shown in FIGS. 6, B–D. The positive staining for BrdU reveals high proliferative activity in papilla of the hair and the basal compartment of the seminiferous epithelium (FIGS. 6, B and C). Staining for alpha smooth muscle actin revealed full differentiation of peritubular cells at all time points analyzed (FIG. 6D). The presence of round and elongated spermatids highlights the completion of the first round of spermatogenesis at Week 4 (FIGS. 6, C and D). Whereas at Weeks 12 and 16 almost all seminiferous tubules contained meiotic germ cells, the number of seminiferous tubules containing spermatids increased to only about 40%, and the number of fully matured germ cells remained low. Starting at Week 4, dilation of the seminiferous tubule lumen became more prominent (FIG. 6B)

Generation of Progeny

Retrieval of sperm from the grafts in combination with assisted fertilization resulted in the generation of live offspring (FIG. 5D). The sperm obtained from the testicular grafts showed a normal fertilizing ability for extracted sperm samples; 80% and 50% of the activated oocytes reached the two- and four-cell stage, respectively. Control experiments using epididymal sperm resulted in 88% and 65% success rates, respectively. From a total of 312 oocytes that were manipulated and allowed to grow in vitro, 94 (30.1%) formed blastocysts by 96 h. A total of 7 pups were produced from two of the four recipients (one pup died after birth; three females and three males grew to maturity). The male and female mice generated from grafted sperm showed normal fertility in mating experiments.

Hormonal Changes in Grafted Animals

Figure 7:
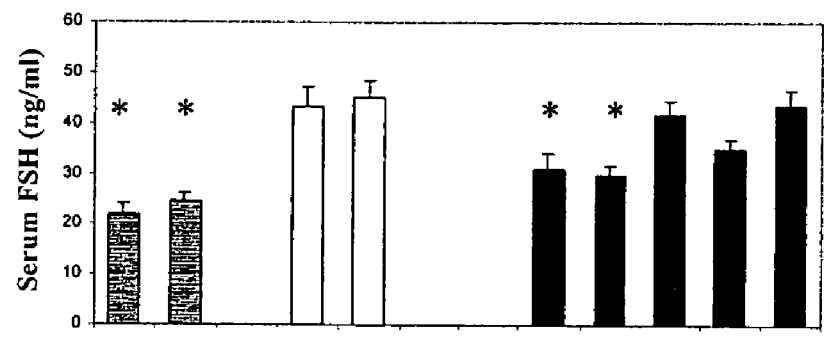
Figure 7:
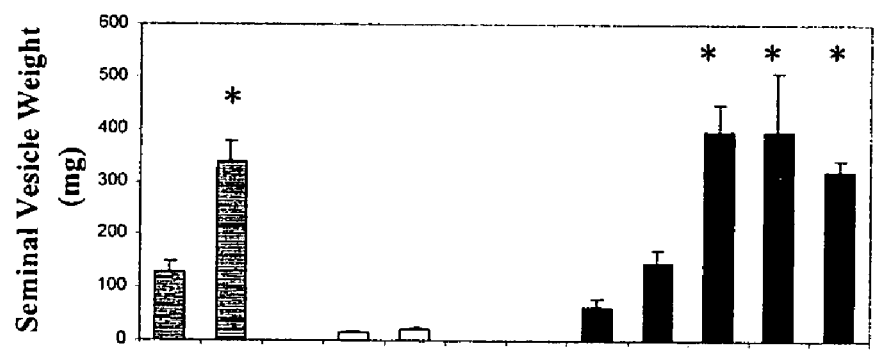
Figure 7:
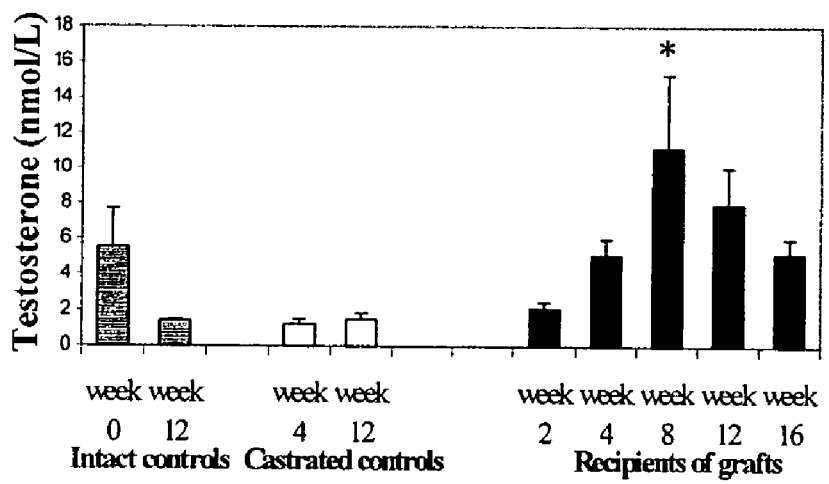

FSH levels were two-fold higher in castrated compared with intact mice (FIG. 7). Grafted animals showed intermediate FSH levels at weeks 2, 4, and 12 and elevated levels close to the castrated range at weeks 8 and 16. From week 8 onward, seminal vesicle weights were maintained in the adult range. Normal adult levels of serum testosterone indicated fully functional steroidogenesis in the grafts leading to restoration of physiological levels of androgens in the castrated host (FIG. 7).

Discussion

In the present study, it is shown that ectopic grafting is a simple and powerful approach for achieving full functional development of neonatal testicular tissue. These results extend the data set forth in Example 1, showing that ectopic grafting of neonatal mouse testicular tissue into immunodeficient hosts leads to the initiation/restoration of spermatogenesis and steroidogenesis. Grafting allows the generation of sperm with full fertilizing potential and therefore can be used to preserve fertility. Ectopic grafting of neonatal testicular tissue can be used to generate gametes from animals that have died before reaching puberty. These data are in concordance with a recent report showing that homotopic transplantation can also be successfully applied to generate offspring using assisted fertilization techniques (Shinohara T, et al. Hum Reprod 2002; 17:3039–3045). These findings open new avenues for studying and preserving fertility in endangered species or in patients undergoing fertility-compromising therapies.

Ectopic testicular grafting might also be useful in several areas of basic research. For example, it allows sperm production and generation of offspring from neonatally lethal transgenic or mutant mouse models, as was proposed for female mice after ovarian grafting (Shaw J M, et al. Methods Mol Biol 2002; 180:229–251) It also provides an experimental approach that extends the use of testicular grafting in a mouse lacking connexin 43 (Roscoe W A, et al. Biol Reprod 2001; 65:829–838), allowing analysis of the capacity for testicular differentiation and meiosis and testing for fertility. Detailed histological analysis revealed that spermatogenesis was complete in the graft, peritubular cells were differentiated, and premeiotic germ cells were proliferating intensively. The grafted tissue developed up to the level of qualitatively full spermatogenesis from neonatal testes with seminiferous cords containing peritubular cells, Sertoli cells, and gonocytes as the most advanced germ cells. Sperm collected from the grafted testicular tissue and microinjected into mouse oocytes gave rise to embryos that developed to term. Fertilization was also achieved using frozen-thawed sperm preparations. When the pups born from these procedures grew to maturity, the three males and three females were used for breeding. Their normal fertility indicates that no major damage to the germline could be attributed to the grafting process or the ectopic location of the male gonad. The exocrine function of generating gametes and the endocrine function were restored in the grafted testicular tissue. Serum FSH and serum androgen concentrations and the growth of seminal vesicles in castrated recipient mice indicated that the grafts were actively secreting hormones. The s.c. testicular tissue was able to establish partial to full feedback when compared with intact and castrated controls. An intermediate level of FSH at weeks 4, 8, and 12 compared with normal and castrated controls was conserved. This finding indicates that the seminiferous epithelium in the testicular grafts controlled the serum FSH levels and that the feedback established from the graft was strong enough to suppress significantly FSH release from the pituitary. The increase in FSH levels at weeks 12 and 16 parallels the increasing damage to the seminiferous epithelium. Changes in serum FSH levels therefore can be used to determine the most promising time for sperm retrieval from the grafted testicular tissue. This evidence indicates that the best time point for retrieval of mouse sperm after s.c. grafting is between weeks 4 and 8, when the first wave of spermatogenesis is completed but the damage to the seminiferous epithelium is not yet pronounced. Androgen production was restored in all mice receiving testicular grafts. Although the serum testosterone levels fluctuated markedly, the weight of the seminal vesicle was a more stable indicator of androgen action. In contrast to FSH, androgen secretion appeared to be similar to that of normal animals and did not change significantly with longer grafting periods. Androgen levels remained in the high normal range when FSH levels increased, suggesting that the spermatogenic failure in the tubular compartment did not have a profound influence on the interstitial cells and that the feedback mechanisms for both gonadotropins are widely independent in the grafted testicular tissue. Leydig cells appeared functionally normal, and their morphology revealed an intact and normal cellular organization. In light of these findings, grafting of testicular tissue is a useful experimental tool for androgen substitution. The possibility of grafting testicular tissue from different species and the experimental manipulation of grafting different quantities of testicular tissue or to pretreat the testicular tissue prior to grafting suggest elegant opportunities for studying basic endocrine mechanisms controlling testis growth and generating balanced feedback controls between the pituitary cells and the testicular cells.

Although most of the seminiferous tubules showed some degree of spermatogenic recovery, as early as Week 4 the luminal space enlarged, indicating an accumulation of fluid. At the same time, premature sloughing of germ cells occurred.

Spermatogenesis did not reach quantitatively normal levels in the grafted tissue, and many seminiferous tubules showed some degree of damage to the seminiferous epithelium. These histological defects are very similar to those occurring after efferent duct ligation or in the estrogen receptor knockout mouse (Lee K H, et al. Biol Reprod 2000; 63:1873–1880; Hess R A, et al. J Androl 2000; 21:107–121). In both cases, a blockade of efferent ducts causes the defect that finally leads to complete testicular degeneration. It is therefore reasonable to conclude that the obvious absence of efferent ducts in the grafted tissue and the accumulation of fluid secreted into the seminiferous tubules account for the defects leading to a disturbance of spermatogenesis. This atrophy of testicular tissue was quite specific for mouse grafts only. Neonatal testicular tissue from nonrodent species (i.e., pig, goat, marmoset) was used in previous studies, and no or minimal signs of atrophy were observed. Therefore the regulation of seminiferous fluid production and resorbtion is better balanced in these species. In support of this, several mouse grafts containing intact efferent ducts and adjacent epididymal tissue were observed. These grafts showed no or very few atrophic seminiferous tubules. These findings indicate that the high resorbtive activity of the efferent ductules prevents fluid accumulation in the grafts and allows normal spermatogenesis to persist for long periods of time. Ectopic grafting of neonatal testes leads to induction of complete spermatogenesis and endocrine function and therefore constitutes an experimental tool for fertility preservation and hormone replacement.

EXAMPLE III

Development of Porcine Embryos Following Intracytoplasmic Sperm Injection of Frozen-thawed Sperm from Neonatal Pig Donors Methods of the current invention provide a new alternative for preservation of the male germ line in prepubertal males. Immature testicular tissue can be cryopreserved for later xenotransplantation, and maturation, and the sperm produced thereby may be used for fertilization. Cryopreservation has the advantage of maintaining structural integrity, and providing the compatible microenvironment needed for completion of spermatogenesis after xenotransplantation. Alternatively, sperm produced by the method of this invention may be cryopreserved after harvesting.

This example demonstrates that viable embryos can be produced in species other than mice, following intracytoplasmic sperm injection of previously cryopreserved sperm produced by the methods of the instant invention.

Porcine embryos were successfully developed following ICSI of frozen thawed sperm produced in this system from neonatal pig donors. The injected oocytes were either fixed to determine fertilization processes (n=89, in 5 replications) or were allowed to develop in vitro (n=143, in 4 replications). It was concluded that these xenogeneic porcine sperm were fertilization competent (20–30% vs. 40–50% from control ejaculated sperm) and the resultant embryos could develop to the blastocyst stage (5–10% vs. 20–30% in controls). The lower rates of fertilization and development could be attributed to the fact that the sperm isolated from the xenografts do not undergo epididymal maturation.

These methods can be used to preserve the germline in prepubertal boys undergoing cancer therapies. These methods may also be used to salvage genetic material from superior or endangered animals which are sexually immature and cannot be maintained for sperm production. Grafting of testis tissue from experimental animal strains will also provide a tool to study germ cell development, or to produce gametes and subsequent progeny from animals with poor viability, such as neonatal lethal transgenic, mutant or cloned animals.

EXAMPLE IV

Xenograft of Neonatal Primate Tissue into Mice

Little is known about the mechanisms that govern the timing of testicular maturation. In the Examples above, completion of spermatogenesis in testis tissue from immature pigs and goats grafted into host mice is reported. This technique not only provides a previously unavailable system to obtain sperm from immature animals, but also serves as a model for the study of spermatogenesis and testicular maturation in animals. Provided herein is further evidence of the diverse applicability of the instant method. The following example describes engraftment, and subsequent maturation of immature monkey testes tissue.

Xenografting Immature Primate Testes Tissue into Mice

Xenografting of testis tissue from different species into host mice is a powerful tool for the study and manipulation of spermatogenesis. LH receptor (LHR) is the target for both LH and chorionic gonadotropin (CG). Activation of LHR by LH is believed to have a crucial role in male puberty and normal spermatogenesis. The common marmoset (*Callithrix jacchus*) is known to constitutively express a unique isoform of LHR that lacks exon 10. Evidence from hypogonadal men with a deletion of exon 10 indicates that this receptor is not responsive to LH but can be activated by exogenous CG. Therefore, in the marmoset an alternative system appears to maintain normal spermatogenesis by compensating for the lack of response to LH. The objective of this study was to investigate the functional importance of the LHR for spermatogenesis by allowing the immature marmoset testes to develop as xenografts in comparison to those of the rhesus macaque (*Macaca mulatta*), a primate with complete LHR. Small fragments of testis tissue from immature marmoset and rhesus were grafted under the back skin of castrated immunodeficient mice (n=5/donor species). Graft survival and growth were observed for both donor species and proliferation of Sertoli cells and premeiotic differentiation of germ cells were evident by 4.5 months after transplantation. In xenografts from both species, initiation of development and germ cell differentiation into spermatocytes started at about the same time.

However, by 7-month post-grafting, complete spermatogenesis was only observed in the rhesus, while in the marmoset grafts very few spermatocytes remained as the most advanced type of germ cells. In contrast, in intact animals the time required for complete spermatogenesis is considerably shorter for the marmoset (15 months) than the rhesus (2.5 years). These results indicate that 1) normal LH-LHR interaction is required for postmeiotic differentiation of germ cells, 2) murine LH is able to fully support rhesus monkey spermatogenesis, and 3) for completion of spermatogenesis, the marmoset is likely to have an alternative to the LH-LHR system. Fortunately, humans do not appear to possess this alternative to the LH-LHR system. Since complete rhesus spermatogenesis can occur in the mouse host, testis xenografting has great potential for the study of primate spermatogenesis and to examine underlying mechanisms crucial for the control of fertility.

EXAMPLE V

Xenografting of Testis Tissue from Neonatal Monkeys and Sheep into Mice Accelerates Testicular Maturation and Sperm Production The disclosed methods may also be used to produce accelerated testicular development.

Xenografting of Testis Tissue from Immature Rhesus Macaques as a Model for the Study of Primate Spermatogenesis Fragments of testis tissue from 2 sexually immature, 13-month-old rhesus macaques were grafted under the back skin of 12 castrated male SCID mice (8 fragments/mouse). At 6, 12, 18 and 24 weeks, grafts from 3 recipients/donor were analyzed. At the time of grafting, spermatogenic cords contained gonocytes. After 6 weeks, spermatogonia were visible in expanded tubules. 12 and 18 weeks after grafting, round spermatids were the most advanced germ cell type. Mature sperm were observed at 24 weeks. Control tissue from 2- and 3-year-old macaques showed no evidence of spermatogenic differentiation. These results indicate that complete primate spermatogenesis can occur in the mouse host. Importantly, maturation of testis tissue was accelerated compared to the donor species. Complete primate spermatogenesis from immature donors in a mouse host has far reaching potential for the study of spermatogenesis and the preservation of genetic material.

Sperm produced from sexually immature animals could be used to propagate the genetics of animals that do not reach puberty.

Engraftment from Rams

Testes from 1-wk-old Suffolk ram lambs were cut into small fragments (about 1 mm$^3$ each) and eight fragments were grafted under the back skin of each castrated immunodeficient host mouse (n=10). Histological examination of the testis xenografts was performed between 2 and 7 months post-transplantation. At the time of grafting, the seminiferous cords of the donor testis tissue contained only immature Sertoli cells and gonocytes. At 2 month after grafting, extensive tubular expansion was evident caused by the proliferation of Sertoli cells and tubular lumen formation. Seminiferous epithelium at this time point contained spermatocytes and round spermatids as the most advanced types of germ cells. By 3 months after transplantation, xenografts of testis tissue had already completed spermatogenesis and mature sperm were present. In contrast, in intact Suffolk rams, first testicular sperm appear after 5–6 months of age. Spermatogenesis was sustained in the remaining testis xenografts that remained in the mouse hosts for up to 7 months. In addition, the weight of the seminal vesicles in the castrated host mice was restored to pre-castration values, indicating that xenografts were capable of releasing biologically active testosterone. These results demonstrate the potential of xenografting to achieve full spermatogenesis in testis tissue from neonatal sheep. Furthermore, development in the mouse host accelerated the onset of sperm production by at least 2 months. This indicates that the timing of testicular maturation is not inherent to the donor species but can readily be advanced by sufficient gonadotropin stimulation in the mouse host. Testis tissue xenografting provides a unique tool to study the mechanisms governing testicular maturation and spermatogenesis.

The previous examples and description set forth certain embodiments of the invention. It should be appreciated that not all components or method steps of a complete implementation of a practical system are necessarily illustrated or described in detail. Rather, only those components or method steps necessary for a thorough understanding of the invention have been illustrated and described in detail. Actual implementations may utilize more steps or components or fewer steps or components. Thus, while certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for producing sperm in a recipient animal, comprising:
    a) obtaining a graft of testes tissue from a donor animal;
    b) maintaining said graft in a suitable culture medium until transplant;
    c) implanting said graft ectopically under the skin of an immunocompromised animal;
    d) maintaining said graft in recipient animal so that spermatogenesis may occur so as to produce sperm within graft;
    e) harvesting said sperm from said graft;
    wherein said donor animal and said recipient animal are different species.

2. The method of claim 1, wherein said recipient animal is castrated.

3. The method of claim 1, wherein said suitable medium of step b) is a cryopreservation medium and said graft is cryopreserved and thawed prior to performance of steps c)–e).

4. The method of claim 1, further comprising a step f) of cryopreserving said sperm.

5. The method of claim 1, further comprising a step f) of injecting said sperm into an oocyte.

6. The method of claim 1, wherein said recipient animal is selected from the group consisting of an athymic mouse, a SCID mouse, and a Rag mouse.

7. The method of claim 1, wherein said donor animal is selected from the group consisting of a mouse, a rat, a dog, a cat, a horse, a sheep, a bull, a llama, a pig, a non-human primate, a human, a rare or endangered species, a domestic animal, and a livestock animal.

8. The method of claim 1, wherein said donor animal is a pre-pubescent male and said graft is harvested prior to administration of chemotherapy, or other fertility impairing treatment.

9. The method of claim 1, wherein said graft is obtained from a donor mammal having a lethal phenotype.

10. A method for identifying the effect of an agent on germ cell differentiation and/or spermatogenesis, comprising:
    a) obtaining a graft of testis tissue from a donor animal;
    b) maintaining said graft in a suitable culture medium until transplant;
    c) implanting said graft ectopically under the skin of a pair of immunocompromised recipient animals;
    d) administering an agent suspected of affecting germ cell differentiation and/or spermatogenesis to one of said pair of recipient animals;
    e) maintaining said grafts in said recipient animals so that germ cell differentiation and/or spermatogenesis may occur;
    f) harvesting the grafts from each of said recipient animals; and g) determining the difference in germ cell differentiation and/or spermatogenesis in the graft obtained from the treated recipient animal compared to the graft obtained from the untreated recipient animal to identify effects of said agent on germ cell differentiation and/or spermatogenesis;

wherein said donor animal is of a different species than the recipient animals.

11. The method of claim 10, wherein sperm quality from within the graft is assessed via the determination of at least one of sperm viability, sperm number, sperm morphology, and capacity to initiate fertilization.

12. A method for identifying the effect of an agent on germ cell differentiation and/or spermatogenesis, comprising:
  a) administering an agent suspected of affecting germ cell differentiation and/or spermatogenesis to one of a pair of donor animals;
  b) obtaining a graft of testis tissue from each of said donor animals;
  c) maintaining said grafts in a suitable culture medium until transplant;
  d) implanting said grafts ectopically under the skin of an immunocompromised recipient animal;
  e) maintaining said grafts in said recipient animal so that germ cell differentiation and/or spermatogenesis may occur;
  f) harvesting the grafts from said recipient animal; and
  g) determining the difference in germ cell differentiation and/or spermatogenesis in the graft derived from treated the treated donor animal compared to the graft derived from the untreated donor animal to identify the effect of said agent on germ cell differentiation and/or spermatogenesis;

wherein said donor animals are of a different species than the recipient animal.

13. The method of claim 12, wherein sperm quality from within the graft is assessed via the determination of at least one of sperm viability, sperm number, sperm morphology, and capacity to initiate fertilization.

* * * * *